United States Patent
Chen et al.

(10) Patent No.: US 9,266,802 B2
(45) Date of Patent: *Feb. 23, 2016

(54) HYDROCONVERSION OF RENEWABLE FEEDSTOCKS

(71) Applicant: Chevron U.S.A. Inc., San Ramon, CA (US)

(72) Inventors: Cong-Yan Chen, Kensington, CA (US); Alexander E. Kuperman, Orinda, CA (US); William James Cannella, Orinda, CA (US); Theodorus Ludovicus Michael Maesen, Moraga, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 386 days.

This patent is subject to a terminal disclaimer.

(21) Appl. No.: 13/708,811

(22) Filed: Dec. 7, 2012

(65) Prior Publication Data

US 2014/0163249 A1 Jun. 12, 2014

Related U.S. Application Data

(63) Continuation-in-part of application No. 13/315,611, filed on Dec. 9, 2011, now Pat. No. 8,704,007, and a continuation-in-part of application No. 13/315,774, filed on Dec. 9, 2011, now Pat. No. 8,865,949, and a (Continued)

(51) Int. Cl.
*C07C 29/149* (2006.01)
*C10G 3/00* (2006.01)
*C11C 3/12* (2006.01)
(Continued)

(52) U.S. Cl.
CPC ............... *C07C 29/149* (2013.01); *C10G 3/46* (2013.01); *C10G 3/50* (2013.01); *C10G 45/58* (2013.01); *C10G 50/02* (2013.01); *C10G 69/14* (2013.01); *C11C 3/00* (2013.01); *C11C 3/123* (2013.01);
(Continued)

(58) Field of Classification Search
None
See application file for complete search history.

(56) References Cited

U.S. PATENT DOCUMENTS 5,366,658 A 11/1994 Hoppe et al.
7,544,850 B2 6/2009 Goze et al.
(Continued)

OTHER PUBLICATIONS

PCT International Search Report and Written Opinion, International Application No. PCT/US2012/068621, dated Mar. 29, 2012.

(Continued)

*Primary Examiner* — Yate K Cutliff
(74) *Attorney, Agent, or Firm* — Hanh T. Pham; Michael D. Ross

(57) ABSTRACT

A hydroconversion process comprises contacting a feedstock comprising renewable materials under hydroprocessing conditions with a promoted catalyst selected from a self-supported catalyst, a supported catalyst and combinations thereof, wherein the reaction conditions can be tailored to directly convert the renewable feedstock to the desired product(s) including fatty alcohols, esters, normal paraffins, or combinations thereof. The catalyst comprising at least a Group VIB metal selected from molybdenum and tungsten, a Group VIII metal selected from cobalt and nickel to convert the feedstock into any of fatty alcohols, esters, and normal paraffins. In some embodiments, the process further comprising additional steps to generate various desirable products, including α-olefins (or PAO, by dehydrating the fatty alcohol products), lubricants and bright stocks (from the oligomerizing of the PAO), and Group 3 lubricants (from co-oligomerizing of the PAO with some short chain olefins).

32 Claims, 2 Drawing Sheets

Related U.S. Application Data continuation-in-part of application No. 13/315,575, filed on Dec. 9, 2011, now Pat. No. 8,884,077, and a continuation-in-part of application No. 13/315,683, filed on Dec. 9, 2011, now abandoned, and a continuation-in-part of application No. 13/315,650, filed on Dec. 9, 2011, now Pat. No. 9,035,115, and a continuation-in-part of application No. 13/315,729, filed on Dec. 9, 2011.

(51) Int. Cl.

| | | |
|---|---|---|
| *C11C 3/00* | (2006.01) | |
| *C10G 45/58* | (2006.01) | |
| *C10G 50/02* | (2006.01) | |
| *C10G 69/14* | (2006.01) | |

(52) U.S. Cl.
CPC .... *C10G 2300/1022* (2013.01); *C10G 2400/10* (2013.01)

(56) References Cited

U.S. PATENT DOCUMENTS

| | | | |
|---|---|---|---|
| 7,667,059 B2 | 2/2010 | Sakamoto et al. | |
| 7,888,542 B2 | 2/2011 | Koivusalmi et al. | |
| 7,910,761 B2 * | 3/2011 | Maesen et al. | 556/28 |
| 8,097,740 B2 | 1/2012 | Miller | |
| 8,119,847 B2 * | 2/2012 | Dindi et al. | 585/240 |
| 8,324,438 B2 | 12/2012 | Brandvold et al. | |
| 2006/0207166 A1 | 9/2006 | Herskowitz et al. | |
| 2007/0161832 A1 | 7/2007 | Myllyoja et al. | |
| 2009/0166256 A1 | 7/2009 | Lewis et al. | |
| 2009/0255171 A1 | 10/2009 | Dumesic et al. | |
| 2010/0263263 A1 | 10/2010 | O'Rear | |
| 2011/0015459 A1 | 1/2011 | Aalto et al. | |
| 2011/0047862 A1 | 3/2011 | Mayeur et al. | |
| 2011/0155636 A1 | 6/2011 | Hanks et al. | |
| 2012/0000824 A1 | 1/2012 | Dougherty et al. | |
| 2012/0016167 A1 | 1/2012 | Hanks | |
| 2012/0053099 A1 | 3/2012 | Zhou et al. | |
| 2012/0216450 A1 | 8/2012 | Dupassieux et al. | |
| 2012/0283151 A1 | 11/2012 | Espagne et al. | |

OTHER PUBLICATIONS

U.S. Appl. No. 13/315,575, filed Dec. 9, 2011, Chen.
U.S. Appl. No. 13/315,611, filed Dec. 9, 2011, Chen.
U.S. Appl. No. 13/315,650, filed Dec. 9, 2011, Chen.
U.S. Appl. No. 13/315,683, filed Dec. 9, 2011, Chen.
U.S. Appl. No. 13/315,729, filed Dec. 9, 2011, Chen.
U.S. Appl. No. 13/315,774, filed Dec. 9, 2011, Chen.

* cited by examiner

HYDROCONVERSION OF RENEWABLE FEEDSTOCKS

CROSS-REFERENCE TO RELATED APPLICATIONS

This application claims priority as a continuation-in-part to U.S. patent application Ser. Nos. 13/315,611; 13/315,774; 13/315,575; 13/315,729; 13/315,650; and 13/315,683, all with a filing date of Dec. 9, 2011. This application claims priority as a continuation-in-part to and benefits from the foregoing, the disclosures of which are incorporated herein by reference.

TECHNICAL FIELD

The application relates generally to a process for converting renewable feedstocks to oleochemicals such as fatty alcohols, esters, and normal paraffins, by contacting the feedstock with at least a multi-metallic catalyst under hydroprocessing conditions.

BACKGROUND

Fossil fuels are a finite, non-renewable resource formed from decayed plants and animals that have been converted to crude oil, coal, natural gas, or heavy oils by exposure to heat and pressure in the earth's crust over hundreds of millions of years. However, as the world's petroleum resources are depleting coupled with its ever-increasing prices, many industries worldwide have been looking into renewable/sustainable raw materials ("bio-resources") to replace petroleum-based materials in their manufacturing processes.

Industrial oleochemicals are useful in the production of surfactants, lubricants, fuels, plastics, and the like. Oleochemicals include, but are not limited to, fatty alcohols, esters and paraffins. Providing efficient processes for directly converting renewable materials into such products would be highly desirable.

A prior art approach to convert bio-resources such as lipids (e.g., vegetable oil, animal fat, etc.) to high value products such as jet/diesel fuels (paraffins) is via alkali catalyzed reaction in the presence of an alcohol, generating esters such as long chain alkyl esters or fatty acid methyl ester (FAME). Hydroprocessing is another approach to covert bio-resources to useful products. However, in US Patent Publication No. 2009/0166256, it is disclosed that with biocomponent feedstocks, e.g., vegetable oils and animal fats which typically contain triglycerides and fatty acids, the large triglyceride and fatty acid molecules in biocomponent feedstocks may competitively adsorb on and block active sites of hydrotreating catalysts. There is a need for catalysts having the appropriate morphology, structure, and optimum catalytic activity for high yield conversion of renewable feedstock into high value products.

Base oils are commonly used for the production of process oils, white oils, metal working oils, and lubricants for use in automotives, industrial applications, and the like. It is increasingly difficult to produce lubricants from conventional mineral oils to meet certain standards in the automotive industry. There is a need for an improved process to make lubricants and bright stocks with renewable feedstock as the originating source.

SUMMARY

In one aspect, there is provided catalytic conversion process comprising contacting a renewable feedstock, under hydroprocessing conditions, with at least a self-supported catalyst or a supported catalyst to form an effluent and recovering a hydrocarbon fraction comprising normal paraffins from the effluent, wherein the hydroprocessing conditions include a temperature of from 446° F. to 752° F. (230° C. to 400° C.) and a total reaction pressure of from 50 to 3000 psig (0.35 to 20.7 MPa gauge).

In another aspect, there is provided a catalytic conversion process comprising contacting a renewable feedstock, under hydroprocessing conditions, with at least a self-supported catalyst or a supported catalyst to form an effluent and recovering an aliphatic monoester fraction from the effluent, wherein the hydroprocessing conditions include a temperature of from 302° F. to 554° F. (150° C. to 290° C.) and a total reaction pressure of from 50 to 3000 psig (0.35 to 20.7 MPa gauge).

In yet another aspect, there is provided a hydrocarbon conversion process comprising contacting a renewable feedstock, under hydroprocessing conditions, with at least a self-supported catalyst or a supported catalyst to form an effluent and recovering a fatty alcohol fraction from the effluent, wherein the hydroprocessing conditions include a temperature of from 302° F. to 554° F. (150° C. to 290° C.) and a total reaction pressure of from 50 to 3000 psig (0.35 to 20.7 MPa gauge). The fatty alcohol fraction in one embodiment is further processed forming Guerbet alcohols.

In yet another aspect, there is provided a catalytic conversion process wherein a renewable feedstock is brought into contact with at least with at least a self-supported catalyst or a supported catalyst to form an effluent containing a fatty alcohol, wherein the fatty alcohol is recovered and subsequently dehydrated in a dehydration zone under dehydration conditions to forming an alpha-olefin product.

In one embodiment, the alpha-olefin product formed is oligomerized in an oligomerization zone under oligomerization conditions to form an oligomer. In yet another embodiment, the oligomer formed is hydrogenated forming a base oil, under hydroprocessing conditions including a temperature from 302° F. to 752° F. (150° C. to 400° C.) and a total reaction pressure of from 50 to 3000 psig (0.35 to 20.7 MPa gauge).

In the invention, the promoted self-supported catalyst or the promoted supported catalyst comprises at least a Group VIB metal selected from molybdenum and tungsten, at least a Group VIII metal selected from cobalt and nickel, the promoter being selected from the group of hydroxy-(di)-carboxylic acids with steric configurations and having the structure of:

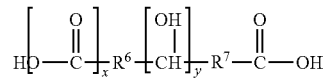

where x is 1 or 0, y is 1 or 0, and $R^6$ or $R^7$ are a saturated, unsaturated, cyclic, acyclic, aromatic, alcoholic, branched or unbranched hydrocarbon group, with $R^6$ or $R^7$ being $(CH_2)_m (CH_2)_n$, with m and n as $\geq 0$ integers.

DETAILED DESCRIPTION

Figure 1:
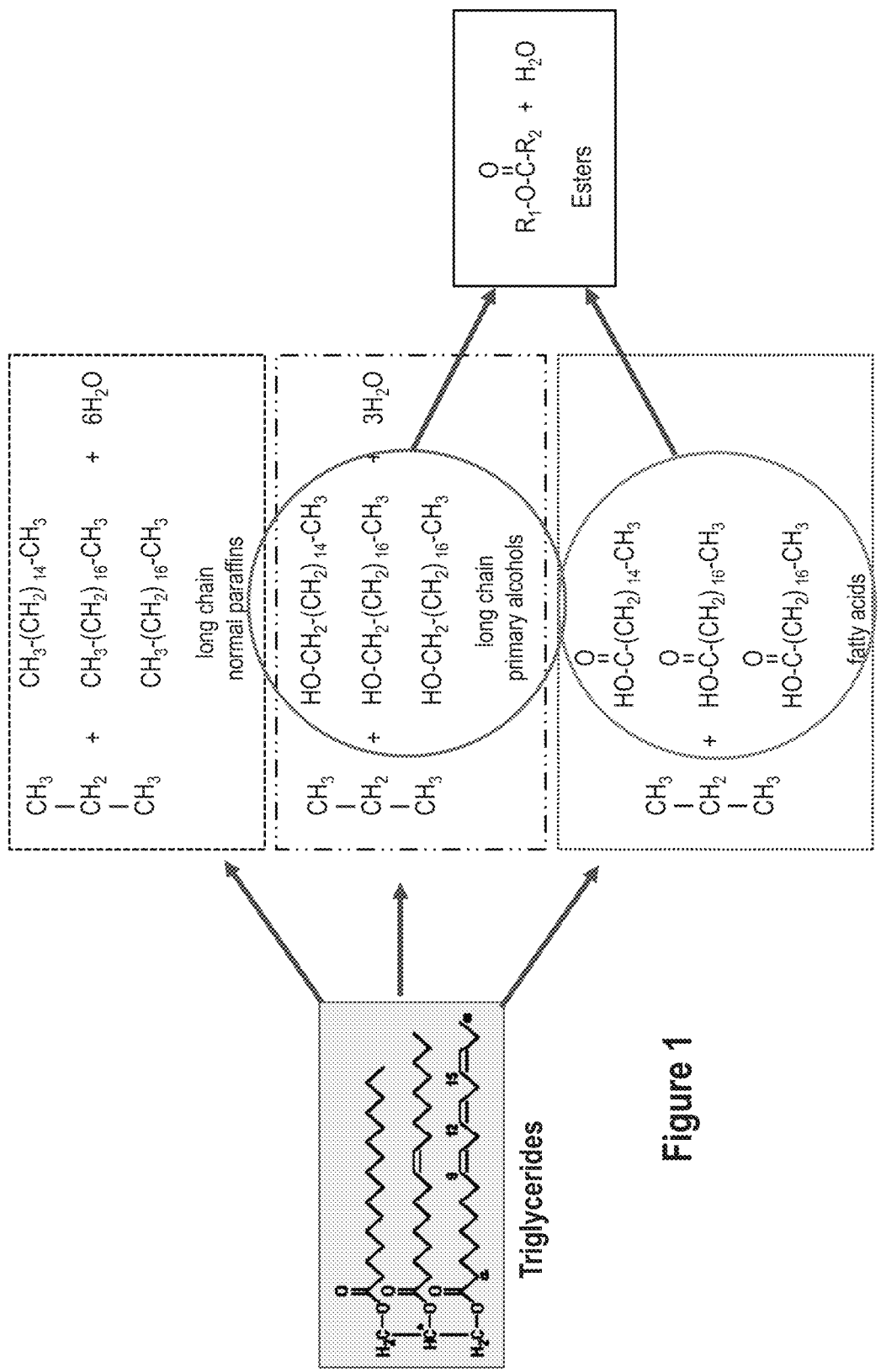
FIG. 1 is a schematic diagram showing the various reaction pathways in the hydroprocessing of a renewable feedstock, e.g., triglycerides, generating various desired products such as long chain normal paraffins, fatty alcohols, fatty acids and esters.

The following terms will be used throughout the specification and will have the following meanings unless otherwise indicated.

"Renewable feedstock" refers to feedstocks other than those obtained from fossil resources such as crude oil, coal, natural gas, sad oil, etc. meaning feedstock derived in part from a biological raw material component such as plant-based material such as vegetable fats/oils, or animal fats/oils, including algae and fish fats/oils. In one embodiment, the renewable feedstock is a triglyceride containing renewable feedstock.

"Oleochemical" refers to a chemical that is biologically-derived, i.e., from a renewable resource of biological origin. Such a term is generally accepted as being exclusive of fossil fuels.

A "middle distillate" is a hydrocarbon product having a boiling range of from 250° F. to 1100° F. (121° C. to 593° C.). The term "middle distillate" includes the jet fuel, kerosene, diesel, heating oil boiling range fractions. It may also include a portion of naphtha or light oil. A "jet fuel" is a hydrocarbon product having a boiling range in the jet fuel boiling range. The term "jet fuel boiling range" refers to hydrocarbons having a boiling range of from 280° F. to 572° F. (138° C. to 300° C.). The term "diesel fuel boiling range" refers to hydrocarbons having a boiling range of from 250° F. to 1000° F. (121° C. to 538° C.). The "boiling range" is the 10 vol. % boiling point to the final boiling point (99.5 vol. %), inclusive of the end points, as measured by ASTM D2887-08 ("Standard Test Method for Boiling Range Distribution of Petroleum Fractions by Gas Chromatography").

"Triglyceride" refers to class of molecules having the general formula (1):

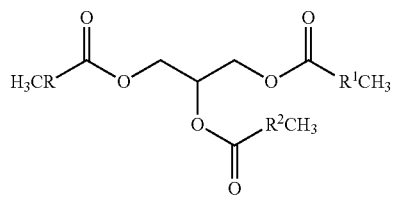

wherein R, $R^1$ and $R^2$ are independently aliphatic residues having from 6 to 22 carbon atoms (e.g., from 8 to 20 carbon atoms, or from 10 to 16 carbon atoms). The term "aliphatic" means a straight (i.e., un-branched) or branched, substituted or un-substituted hydrocarbon chain that is completely saturated or that contains one or more units of unsaturation.

"Fatty alcohol" refers to primary aliphatic alcohols generally having from 8 to 24 carbon atoms per molecule, usually from 8 to 18 carbon atoms.

"Aliphatic monoester" refers to compounds having the general formula (2):

wherein $R^3$ and $R^4$ are independently alkyl moieties. In some embodiments, the aliphatic ester has from 16 to 40 carbon atoms per molecule (e.g., from 18 to 36, or from 20 to 34 carbon atoms). Such esters can be useful as lubricants.

"Paraffin" refers to any saturated hydrocarbon compound, e.g., a paraffin having the formula $C_nH_{(2n+2)}$ where n is a positive non-zero integer.

"Normal paraffin" refers to a saturated straight chain hydrocarbon.

"Isoparaffin" refers to a saturated branched chain hydrocarbon.

"Hydroconversion" can be used interchangeably with the term "hydroprocessing" and refers to any process that is carried out in the presence of hydrogen and a catalyst. Such processes include, but are not limited to, methanation, water gas shift reactions, hydrogenation, hydrotreating, hydrodesulfurization, hydrodenitrogenation, hydrodeoxygenation, hydrodemetallation, hydrodearomatization, hydroisomerization, hydrodewaxing and hydrocracking including selective hydrocracking.

"Isomerizing" refers to catalytic process in which a paraffin is converted at least partially into its isomer containing more branches or the reverse, e.g., a normal paraffin to an isoparaffin. Such isomerization generally proceeds by way of a catalytic route.

"Supported catalyst" refers a catalyst in which the active components, e.g., Group VIII and Group VIB metals or compounds thereof, are deposited on a carrier or support.

"Self-supported catalyst" can be used interchangeably with "unsupported catalyst," or "bulk catalyst," meaning that the catalyst composition is NOT of the conventional catalyst form which has a preformed, shaped catalyst support which is then loaded with metal compounds via impregnation or deposition. In one embodiment, the self-supported catalyst is formed through precipitation. In another embodiment, the self-supported catalyst has a binder incorporated into the catalyst composition. In yet another embodiment, the self-supported catalyst is formed from metal compounds and without any binder.

"Catalyst precursor" in one embodiment refers to a compound containing at least a metal selected from Group IIA, Group IIB, Group IVA, Group VIII metals and combinations thereof (e.g., one or more Group IIA metals, one or more Group IIB metals, one or more Group IVA metals, one or more Group VIII metals, and combinations thereof); at least a Group VIB metal; and, optionally, one or more organic oxygen-containing promoters, and which compound can be used directly in the upgrade of a renewable feedstock (as a catalyst), or can be sulfided for use as a sulfided hydroprocessing catalyst.

"Group IIA" or "Group IIA metal" refers to beryllium (Be), magnesium (Mg), calcium (Ca), strontium (Sr), barium (Ba), radium (Ra), and combinations thereof in any of elemental, compound, or ionic form.

"Group IIB" or "Group IIB metal" refers to zinc (Zn), cadmium (Cd), mercury (Hg), and combinations thereof in any of elemental, compound, or ionic form.

"Group IVA" or "Group IVA metal" refers to germanium (Ge), tin (Sn) or lead (Pb), and combinations thereof in any of elemental, compound, or ionic form.

"Group VIB" or "Group VIB metal" refers to chromium (Cr), molybdenum (Mo), tungsten (W), and combinations thereof in any of elemental, compound, or ionic form.

"Group VIII" or "Group VIII metal" refers to iron (Fe), cobalt (Co), nickel (Ni), ruthenium (Ru), rhodium (Ro), palladium (Pd), osmium (Os), iridium (Ir), platinum (Pt), and combinations thereof in any of elemental, compound, or ionic form.

The Periodic Table of the Elements refers to the version published by the CRC Press in the *CRC Handbook of Chemistry and Physics,* 88th Edition (2007-2008). The names for families of the elements in the Periodic Table are given herein the Chemical Abstracts Service (CAS) notation.

"Conversion" refers to the amount of triglycerides in the feed that is converted to compounds other than triglycerides. Conversion is expressed as a weight percentage based on triglycerides in the feed. "Selectivity" is expressed as a weight percent based on converted triglycerides.

"Noble metal" refers to a metal selected from ruthenium, rhodium, palladium, silver, osmium, iridium, platinum, and gold.

"Promoter" refers to an organic agent that interacts strongly with inorganic agents (either chemically or physically) in a reaction to form a catalyst or a catalyst precursor, leading to alterations in the structure, surface morphology and composition, which in turn results in enhanced catalytic activity.

"Presulfiding" or "presulfided" refers to the sulfidation of a catalyst precursor in the presence of a sulfiding agent such as $H_2S$ or dimethyl disulfide (DMDS) under sulfiding conditions, prior to contact with a feedstock in an upgrade process.

Feedstock:

The feedstock consists essentially of a renewable feedstock (>99 wt. %), with less than 1 wt. % petroleum feed in one embodiment; less than 2 wt. % petroleum feed in a second embodiment; and less than 5 wt. % petroleum feed in a third embodiment. The feedstock is a mix of a renewable source and a petroleum feed in another embodiment, with up to 50 wt. % petroleum feedstock. The amount of petroleum feedstock ranges from 1 to 99 wt. %, with the remainder renewable feedstock in one embodiment; from 10 to 90 wt. % in a second embodiment; and from 20 to 80 wt. % in a third embodiment. In another embodiment, the feedstock is a pure renewable feedstock (consisting only of a renewable feedstock), with no petroleum feed included.

The renewable feedstocks that can be used include any of those which comprise triglycerides. The feedstock generally originates from a biomass source selected from crops, vegetables, microalgae, animal fats, and combinations thereof. The feedstock generally comprises at least 25 wt. % triglycerides (e.g., at least 50 wt. %, 75 wt. %, 90 wt. %, or 95 wt. % triglycerides). Generally, any biological source of lipids can serve as the biomass from which the feedstock can be obtained. Exemplary feedstocks include, but are not limited to canola oil, coconut oil, palm oil, palm kernel oil, peanut oil, rapeseed oil, soybean oil, and the like.

Reaction Pathways:

In the conversion of renewable feedstock such as triglycerides, the reaction pathways in one embodiment are as shown in FIG. 1, with the formation of various products such as long chain normal paraffins (jet and diesel range materials), long chain primary alcohols, and fatty acids. Depending on the reaction conditions, esters can also be formed, as the reaction product of the long chain primary alcohol and fatty acid products.

In one embodiment, the invention relates to tailoring reaction conditions to optimize (i.e., maximizing) the formation of specific products, e.g., paraffins, alcohols, and/or esters, employing a promoted hydroprocessing catalyst with the promoter selected from the group of hydroxy-(di)-carboxylic acids with steric configurations, having the structure:

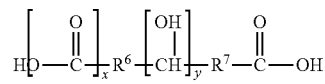

where x is 1 or 0, y is 1 or 0, and $R^6$ or $R^7$ are a saturated, unsaturated, cyclic, acyclic, aromatic, alcoholic, branched or unbranched hydrocarbon group, with $R^6$ or $R^7$ being $(CH)_{2m}(CH_2)_n$, with m and n as >=0 integers. "Hydroxy-(di)-carboxylic acids" means either hydroxylcarboxylic acids or hydrodicarboxylic acids. Examples include but are not limited to (R,S)-malic acid HOOC—$CH_2$—CHOH—COOH, or maleic acid HOOC—CH=CH—COOH. The promoter in one embodiment is present in an amount of at least 0.05 molar times of the total number of moles of the metals of Group VIB and at least another metal present, e.g., a Group VIII metal. In one embodiment, the promoter is present in an amount ranging from 0.05 to about 1000 molar times of the total number of moles of metals.

With respect to the formation of paraffins (jet/diesel range hydrocarbons) from triglycerides, there are three basic reaction pathways:

Hydrodecarboxylation:

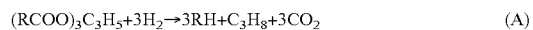
$(RCOO)_3C_3H_5 + 3H_2 \rightarrow 3RH + C_3H_8 + 3CO_2$ (A)

Hydrodecarbonylation:

$(RCOO)_3C_3H_5 + 6H_2 \rightarrow 3RH + C_3H_8 + 3CO + 3H_2O$ (B)

Hydrodeoxygenation:

$(RCOO)_3C_3H_5 + 12H_2 \rightarrow 3RCH_3 + C_3H_8 + 6H_2O.$ (C)

As shown, the hydrogen consumption varies according to the different reaction pathways. As hydroprocessing progresses in severity, i.e., from hydrodecarboxylation via hydrodecarbonylation to hydrodeoxygenation, the amount of hydrogen consumption increases. The invention further relates to tailoring the reaction conditions to optimize the economy of hydrogen consumption.

Promoted Catalyst—Self-Supported Catalyst:

In one embodiment, the catalyst for the upgrade of renewable feedstock is a promoted self-supported catalyst derived from a catalyst precursor. The catalyst precursor can be a hydroxide or oxide material, prepared from at least a Group VIB metal precursor feed and at least another metal precursor feed. The at least another metal precursor can be used interchangeably with $M^P$, referring to a material that enhances the activity of a catalyst (as compared to a catalyst without the at least another metal, e.g., a catalyst with just a Group VIB metal), with the promoter being present in an amount of at least 0.05 to about 5 molar times of the total number of moles of the metals of Group VIB and at least another metal present, e.g., a Group VIII metal. In one embodiment, the promoter is present in an amount of up to 1000 molar times the total number of moles of the metals.

The self-supported or unsupported catalyst precursor made can be converted into a hydroconversion catalyst (becoming catalytically active) upon sulfidation. However, the self-supported catalyst precursor can be used in the conversion of the renewable feedstock by itself (as a catalyst), or it can be sulfided prior to use, or sulfided in-situ in the presence of sulfiding agents in the reactor. In one embodiment, the self-supported catalyst precursor is used un-sulfided, with or without any addition of sulfiding agents (e.g., $H_2S$) to the reactor system or inherent in the feed, even for the hydroconversion of a feedstock consisting essentially of renewable materials (without any sulfur present in the feed as sulfiding agent).

In one embodiment, a self-supported multi-metallic oxide may also be used. The self-supported multi-metallic oxide comprises at least one Group VIII metal and at least two Group VIB metals. In one embodiment, the ratio of Group VIB metal to Group VIII metal in the precursor ranges from about 10:1 to about 1:10. In another embodiment, the oxide catalyst precursor is represented by the formula: $(X)_b(MO)_c(W)_dO_f$, wherein X is Ni or Co, Mo is molybdenum, W is tungsten, the molar ratio of b:(c+d) is 0.5:1 to 3:1 (e.g., 0.75:1 to 1.5:1, or 0.75:1 to 1.25:1), the molar ratio of c:d is >0.01:1 (e.g., greater than 0.1:1, 1:10 to 10:1, or 1:3 to 3:1), and f=[2b+6 (c+d)]/2. The oxide catalyst precursor further comprises one or more promoters L. In one embodiment, the self-supported catalyst precursor is of the formula $(NiL)_x(Mo_yW_{1-y})O_{(x+3)}$; wherein L refers to one or more promoters; and wherein x:(1−y) is 1.7-2.4; and y is 0.25 to 0.67. The oxide precursor is generated by combining the Group VIB and group VIII metals, forming a product, then subsequently calcining the product formed thereof.

In another embodiment, the catalyst precursor is in the form of a hydroxide compound, comprising at least one Group VIII metal and at least two Group VIB metals. In one embodiment, the hydroxide catalyst precursor is represented by the formula: $A_v[(M^P)(OH)_x(L)''_y]_z(M^{VIB}O_4)$, wherein A is one or more monovalent cationic species; $M^P$ has an oxidation state (P) of either +2 or +4 depending on the metal(s) being employed; L is one or more oxygen-containing promoters, and L has a neutral or negative charge n≤0; $M^{VIB}$ is at least a Group VIB metal having an oxidation state of +6; $M^P:M^{VIB}$ has an atomic ratio between 100:1 and 1:100; v−2+P*z−x*z+n*y*z=0; and 0<v≤2; 0<x≤P; 0<y≤−P/n; 0<z. In one embodiment, the catalyst precursor is charge-neutral, carrying no net positive or negative charge.

In one embodiment, A is selected from the group consisting of an alkali metal cation, an ammonium cation, an organic ammonium cation and a phosphonium cation.

In one embodiment, $M^P$ has an oxidation state of either +2 or +4. $M^P$ is at least one of a Group IIA metal, Group IIB metal, Group IVA metal, Group VIII metal and combinations thereof. In one embodiment, $M^P$ is at least a Group VIII metal with $M^P$ having an oxidation state P of +2. In another embodiment, $M^P$ is selected from Group IIB metals, Group IVA metals and combinations thereof. In one embodiment, $M^P$ is selected from the group of Group IIB and Group VIA metals such as zinc, cadmium, mercury, germanium, tin or lead, and combinations thereof, in their elemental, compound, or ionic form. In another embodiment, $M^P$ is a Group IIA metal compound, selected from the group of magnesium, calcium, strontium and barium compounds. $M^P$ can be in solution or in partly in the solid state, e.g., a water-insoluble compound such as a carbonate, hydroxide, fumarate, phosphate, phosphite, sulfide, molybdate, tungstate, oxide, or mixtures thereof.

In one embodiment, the promoter L has a neutral or negative charge n≤0. Examples of promoters L include but are not limited to carboxylates, carboxylic acids, aldehydes, ketones, the enolate forms of aldehydes, the enolate forms of ketones, and hemiacetals; organic acid addition salts such as formic acid, acetic acid, propionic acid, maleic acid, malic acid, cluconic acid, fumaric acid, succinic acid, tartaric acid, citric acid, oxalic acid, glyoxylic acid, aspartic acid, alkane sulfonic acids such as methanesulfonic acid and ethanesulfonic acid, aryl sulfonic acids such as benzenesulfonic acid and p-toluenesulfonic acid and arylcarboxylic acids; carboxylate containing compounds such as maleate, formate, acetate, propionate, butyrate, pentanoate, hexanoate, dicarboxylate, and combinations thereof.

In one embodiment, $M^{VIB}$ is at least a Group VIB metal having an oxidation state of +6. In another embodiment, $M^{VIB}$ is a mixture of at least two Group VIB metals, e.g., molybdenum and tungsten. $M^{VIB}$ can be in solution or in partly in the solid state. In one embodiment, $M^P:M^{VIB}$ has a mole ratio of 10:1 to 1:10.

In one embodiment, the self-supported catalyst is prepared from a mixed metal sulfide ("MMS") catalyst precursor, characterized by having an optimized Ni:Mo:W composition with a molar ratio of Ni/W of 1.62≤Ni/W≤2.5, a molar ratio of W/Mo is in the range of 0.5≤W/Mo≤6.0, and a molar ratio of Ni/(Mo+W) in the range of 0.57<Ni/(Mo+W)<2.1. In another embodiment, the MMS catalyst precursor comprises nickel, molybdenum and tungsten having relative proportions within a compositional range defined by four points ABCD in a ternary phase diagram, with molar fractions of the four points ABCD defined by $A(Ni_x=0.36, Mo_x=0.41, W_x=0.22)$; $B(Ni_y=0.45, Mo_y=0.36, W_y=0.18)$; $C(Ni_z=0.58, Mo_z=0.06, W_z=0.36)$, and $D(Ni_w=0.68, Mo_w=0.05, W_w=0.27)$. The MMS catalyst precursor can be used for the upgrade of the renewable feedstock directly with or without being pre-sulfided, or with or without any sulfiding agents being present or added to the feedstock.

Further details regarding the description of the catalyst precursor and the self-supported catalyst formed thereof are described in a number of patents and patent applications, including U.S. Pat. Nos. 6,156,695; 6,162,350; 6,274,530; 6,299,760; 6,566,296; 6,620,313; 6,635,599; 6,652,738; 6,758,963; 6,783,663; 6,860,987; 7,179,366; 7,229,548; 7,232,515; 7,288,182; 7,544,285; 7,615,196; 7,803,735; 7,807,599; 7,816,298; 7,838,696; 7,910,761; 7,931,799; 7,964,524; 7,964,525; 7,964,526; 8,058,203; and U.S. Pat. Application Publication Nos. 2007/0090024, 2009/0107886, 2009/0107883, 2009/0107889 and 2009/0111683, the relevant disclosures are included herein by reference.

Embodiments of the process for making the self-supported catalyst precursor are as described in the references indicated above, and incorporated herein by reference. In one embodiment, the first step is a mixing step wherein at least one Group VIB metal precursor feed and at least one another metal precursor feed are combined together in a precipitation step (also called co-gelation or co-precipitation), wherein a catalyst precursor is formed as a gel. The precipitation (or "co-gelation") is carried out at a temperature and pH under which the Group VIB metal compound and at least another metal compound precipitate (e.g., forming a gel). In one embodiment, the temperature is from 25° C. to 350° C. and the pressure is from 0 to 3000 psig (0 to 20.7 MPa gauge). The pH of the reaction mixture can be changed to increase or decrease the rate of precipitation (co-gelation), depending on the desired characteristics of the catalyst precursor product, e.g., an acidic catalyst precursor. In one embodiment, the mixture is left at its natural pH during the reaction step(s). The pH is maintained in the range from 3-9 in one embodiment; and from 5-8 in a second embodiment.

Promoted Catalyst—Supported Catalyst:

In another embodiment, the hydrotreating catalyst is selected from supported catalysts suitable for hydroconversion of renewable feedstocks. Such catalysts comprise at least one metal component selected from Group VIII metals and/or at least one metal component selected from the Group VIB metals. Group VIII metals include iron (Fe), cobalt (Co) and nickel (Ni). Noble metals, such as palladium (Pd) and/or platinum (Pt), can be included in the hydrotreating catalyst. Group VIB metals include chromium (Cr), molybdenum (Mo) and tungsten (W). Group VIII metals can present in the catalyst in an amount of from 0.5 to 25 wt. % (e.g., from 2 to 20 wt. %, 3 to 10 wt. %, 5 to 10 wt. %, or 5 to 8 wt. %) and Group VIB metals can be present in the catalyst in an amount of from 0.5 to 25 wt. % (e.g., from 5 to 20 wt. %, or 10 to 15 wt. %), calculated as metal oxide(s) per 100 parts by weight of total catalyst, where the percentages by weight are based on the weight of the catalyst before sulfiding. The total weight percent of metals employed in the hydrotreating catalyst is at least 5 wt. % in one embodiment. The remainder of the catalyst can be composed of the support material, although optionally other components may be present (e.g., filler, molecular sieve, or the like, or a combination thereof).

The metal components in the supported catalyst can be in the oxide and/or the sulfide form. If a combination of at least a Group VIII and a Group VIB metal component is present as (mixed) oxides, it can be subjected to a pre-sulfiding treatment prior to proper use in hydroprocessing. Suitably, the catalyst usually comprises one or more components of Ni and/or Co and one or more components of Mo and/or W. However, the supported catalyst precursor can be used in the conversion of the renewable feedstock by itself (unsulfided and as a catalyst) with or without any addition of sulfiding agents (e.g., $H_2S$) to the reactor system or inherent in the feed, or it can be pre-sulfided prior to use, or sulfided in-situ in the presence of sulfiding agents in the reactor or in the feed.

The supported catalyst can be prepared by blending, or co-mulling, active sources of the aforementioned metals with a binder. Examples of binders include silica, silicon carbide, amorphous and crystalline silica-aluminas, silica-magnesias, aluminophosphates, boria, titania, zirconia, and the like, as well as mixtures and co-gels thereof. Preferred supports include silica, alumina, alumina-silica, and the crystalline silica-aluminas, particularly those materials classified as clays or zeolitic materials. Especially preferred support materials include alumina, silica, and alumina-silica, particularly either alumina or silica. Other components, such as phosphorous, can be added as desired to tailor the catalyst particles for a desired application. The blended components can then shaped, such as by extrusion, dried and calcined at temperatures up to 1200° F. (649° C.) to produce the finished catalyst. Alternatively, other methods of preparing the amorphous catalyst include preparing oxide binder particles, such as by extrusion, drying and calcining, followed by depositing the aforementioned metals on the oxide particles, using methods such as impregnation. The supported catalyst, containing the aforementioned metals, can then further dried and calcined prior to use as a hydrotreating catalyst.

In one embodiment, the supported catalyst is a hydroprocessing catalyst prepared as disclosed in US20090298677A1, the relevant disclosures are included herein by reference, by depositing onto a carrier having a water pore volume a composition comprising at least a Group VIB metal and at least a Group VIII metal of the Periodic Table of the Elements, optionally a phosphorus-containing acidic component, and at least a promote, deposited onto a carrier having a water pore volume, and then calcining the impregnated carrier at a temperature greater than 200° C. and lower than the decomposition temperature of the promoter. The Group VIB metal in one embodiment is selected from molybdenum Mo and tungsten W. The Group VIII metal is selected from cobalt Co and nickel Ni. The promoter is present in an amount of 0.05 to about 5 molar times of the total number of moles of the metals of Group VIB and Group VIII. In one embodiment, the molar ratio of the Group VIII metal to Group VIB metal is about 0.05 to about 0.75.

In one embodiment, the promoter is selected from the group of hydroxycarboxylic acids, ethylene glycol, glycerol, ethanolamine, polyethylene glycol, hydroquinone, ethylenediamine, ethylenediamine-tetraacetic acid, cysteine, alanine, methionine, gluconic acid, pyridine-2,3-dicarboxylic acid, thiophene-2-carboxylic acid, mercaptosuccinic acid, nicotinic acid, lactose, and acetone-1,3-dicarboxylic acid. In another embodiment, the promoter is selected from hydroxycarboxylic acids such as tartaric acid, malic acid, glyceric acid, citric acid and gluconic acid. In yet another embodiment, the promoter is citric acid.

In one embodiment, the supported catalyst has an average pore size of 1 to 10 nm (e.g., from 5 to 10 nm) and a surface area of from 20 to 400 $m^2/g$ (e.g., from 100 to 300 $m^2/g$).

Reactor System:

The hydroprocessing process for the upgrade of the renewable feedstock can be a single-staged or multiple-staged reactor system. In one embodiment, the process utilizes a single-stage system. The reactor system can be of any reactor type. In one embodiment, the feedstock is processed in a fixed bed reactor. In one embodiment, unreacted triglycerides can be recycled to the reactor of the single-staged reactor system (having only one reactor) or to one of the reactors in the multiple-staged reactor system (having multiple reactors) for further processing to maximize production of the desired product(s).

In one embodiment, the reactor system comprises at least two reactors in series with the different reactors employing the same or different catalysts. In another embodiment, the reactor comprises a single reactor having at least two catalyst zones, with the different catalyst zones employing the same or different catalysts. In a third embodiment, the system is a single reactor containing a single catalyst type, a self-supported catalyst or a supported catalyst.

In one embodiment of a reactor system employing different catalysts, the different catalysts are employed in a layered or stacked bed reactor system. By "layered" or "stacked bed," it is meant that the first catalyst appears in a separate catalyst layer, bed, reactor, or reaction zone, and the second catalyst appears in a separate catalyst layer, bed, reactor, or reaction zone downstream, in relation to the flow of the feed, from the first catalyst. In one embodiment of a stacked bed system, the system comprises about 5-95 vol. % of the first catalyst with the second catalyst comprising the remainder. In a second embodiment, the volume ratio of the first catalyst is about 30-60 vol. %. In a third embodiment, the volume ratio of the first catalyst ranges from 5 to about 50 vol. %. In one embodiment of a stacked bed system, the first catalyst is a supported catalyst, and the second catalyst is a self-supported catalyst.

Hydroprocessing Conditions:

The hydroprocessing conditions can be selected so that an overall conversion rate of triglycerides in the feedstock is at least 20 wt. %, (e.g., at least 50 wt. %, 60 wt. %, 70 wt. %, 80 wt. %, 90 wt. %, or 95 wt. %). Suitable hydroprocessing conditions can include a temperature of from 302° F. to 752° F. (150° C. to 400° C.), e.g., from 383° F. to 464° F. (195° C. to 240° C.), 491° F. to 662° F. (255° C. to 350° C.), or from 491° F. to 563° F. (255° C. to 295° C.); a total reaction pressure of from 50 to 3000 psig (0.35 to 20.7 MPa gauge), e.g., from 800 to 2000 psig (5.5 to 13.8 MPa gauge), or from 1600 to 2000 psig (11.0 to 13.8 MPa gauge); a liquid hourly space velocity (LHSV) of from 0.1 to 5 $h^{-1}$, e.g., from 0.5 to 2 $h^{-1}$; and a hydrogen feed rate of from 0.1 to 20 MSCF/bbl (thousand standard cubic feet per barrel), e.g., from 1 to 10 MSCF/bbl. Note that a feed rate of 10 MSCF/bbl is equivalent to 1781 L H$_2$/L feed.

In one embodiment, the hydroprocessing conditions include a reaction temperature of at least 446° F. (230° C.) and a reaction pressure from 50 to 3000 psig (0.35 to 20.7 MPa gauge) for the liquid effluent having a normal paraffins concentration of at least 90 wt. %.

In another embodiment, the hydroprocessing conditions include a reaction temperature of 302° F. to 554° F. (150° C. to 290° C.) and a total reaction pressure from 50 to 3000 psig (0.35 to 20.7 MPa gauge) for the liquid effluent having a fatty alcohols concentration of at least 5 wt. %. In yet a third embodiment, the hydroprocessing conditions include a temperature of from 302° F. to 554° F. (150° C. to 290° C.) and a total reaction pressure from 50 to 3000 psig (0.35 to 20.7 MPa gauge) for the liquid effluent to have an aliphatic monoesters concentration of at least 5 wt. %.

In addition to the reaction conditions, which can be tailored/optimized for the reaction pathways to selectively proceed, yielding the desired product(s), the type of catalyst is selected as a separate variable or in conjunction with the reaction conditions. A promoted self-supported catalyst can be more active than a promoted supported catalyst. In one embodiment for a layered catalyst system with two different catalyst types, e.g., a combination of promoted self-supported and promoted supported catalyst, the volume ratio of promoted self-supported to promoted supported catalyst is varied depending on the desired products. For example, a promoted self-supported catalyst is more selective than a promoted supported catalyst in a hydrodecarboxylation/hydrodecarbonylation reaction, with a promoted self-supported catalyst being more favorable for reaction pathways (A) and (B) than for (C), and consuming or requiring less hydrogen:

Hydrodecarboxylation:

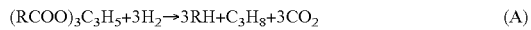

$$(RCOO)_3C_3H_5 + 3H_2 \rightarrow 3RH + C_3H_8 + 3CO_2 \quad \text{(A)}$$

Hydrodecarbonylation:

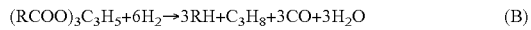

$$(RCOO)_3C_3H_5 + 6H_2 \rightarrow 3RH + C_3H_8 + 3CO + 3H_2O \quad \text{(B)}$$

Hydrodeoxygenation:

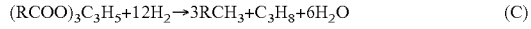

$$(RCOO)_3C_3H_5 + 12H_2 \rightarrow 3RCH_3 + C_3H_8 + 6H_2O \quad \text{(C)}$$

In one embodiment with the use of the promoted self-supported catalyst system, greater than 90% triglyceride conversion is obtained even for a single reactor system. Additionally, greater than 90% conversion is obtained even with the use of unsulfided promoted catalyst precursor in a single reactor system, and without any addition of sulfiding agents to the reactor system.

Reactor temperature is another variable that selectively impacts the reaction pathway and consequently the end products. A higher reactor temperature (e.g., at 500° F. or more) is more favorable for reaction pathways (A) and (B). In the upgrade of a feedstock comprising triglycerides, for example with soybean oil feed which is made mainly of C18- and C16 fatty acids, a higher reactor temperature results in the formation of more n-C17 paraffin (and n-C15 paraffin) over n-C18 paraffin (and n-C16 paraffin) via reaction pathways (A) and (B), with each increase of reactor temperature of 50° F. (e.g., from 500° F. to 550° F.) results in an increase of at least 10% more n-C17 paraffin, other variables being kept constant. Conversely, a lower reactor temperature favors the breaking of the C=O bond in the triglycerides, resulting in more n-C18 (and n-C16) paraffin products. At a reactor temperature of 550° F. or more and a total reaction pressure of 1000 psig or less, there is more of n-C17 paraffin over n-C18 formed.

Another variable that selectively impacts the formation of the end-products is the total reaction pressure, for example again with soybean oil feed which is made mainly of C18- and C16 fatty acids, with lower total reaction pressure favoring reaction pathways (A) and (B), resulting in the formation of more n-C17 paraffin (and n-C15 paraffin) over n-C18 paraffin (and n-C16 paraffin), with a total reaction pressure of 1000 psi or less resulting in an increase of at least 10% more n-C17 paraffin than a total reaction pressure of 1500 psi or more, other variables being kept constant.

In an optimized system to form predominantly long-chain normal paraffins, for example with soybean oil feed which is made mainly of C18- and C16 fatty acids, the reaction temperature is at least 450° F. for a triglyceride conversion rate of at least 85% (i.e., less than 15% unconverted triglycerides), at least 500° F. (260° C.) for a conversion rate of at least 90% triglyceride conversion in one embodiment, at least 95% conversion in a second embodiment, and at least 99% conversion in a third embodiment.

As shown, reaction temperature can be adjusted to accommodate facility process conditions such as available H$_2$ feed. In the reaction pathways to form long-chain normal paraffins, the hydrodeoxygenation reaction consumes four times the amount of H$_2$ required for a hydrodecarboxylation reaction. To accommodate a reduction in available H$_2$ feedstock to the reaction while still obtaining desired jet/diesel end products, the reaction temperature is maintained at a temperature of at least 550° F. in one embodiment and at least 600° F. in a second embodiment. In yet another embodiment and in addition to an increase in the reactor temperature, the total reaction pressure is kept at 1200 psi or less for a combination of excellent conversion yield and optimized production of jet/diesel products (e.g., of at least 90% of the effluent products comprising n-paraffins).

In one embodiment to optimize H$_2$ consumption and/or availability to the upgrade system while still obtaining desired jet/diesel end product distribution, the hydroprocessing conditions can be adjusted by any of: increasing the reactor temperature of at least 50° F., decreasing the reaction pressure of at least 500 psi, and combinations thereof for every reduction in available H$_2$ to the process of 10% to the system, for a minimum amount of H$_2$ at least 4 times the molar ratio of triglycerides in the feedstock. Every increase in reactor temperature of at least 50° F., or every decrease in the total reaction pressure of at least 100 psi results in a reduction in hydrogen consumption in the process of at least 10 SCF/barrel of feedstock in one embodiment, and at least a reduction of hydrogen consumption of at least 20 SCF/barrel of feedstock in a second embodiment.

As shown in FIG. 1, multiple reaction pathways may occur in a reactor system for the conversion of a renewable feedstock (e.g., a vegetable oil with the majority of the fatty acids being triglycerides): a) conversion of triglycerides to n-paraffins; b) conversion of triglycerides to composite fatty acids (which build up the triglycerides); c) production of fatty alcohols which have the same number of carbon atoms in the molecules as these fatty acids; and d) production of esters via the transesterification of the resulting alcohols and fatty acids. All these reactions can simultaneously occur in the reactor system.

The liquid product of the reaction in one embodiment comprises a least one of: paraffins, alcohols, acids, esters (formed from the resulting alcohols and acids), unconverted triglycerides if any, and combinations thereof. The compositions depend on the selected catalyst and the hydroprocessing conditions. Under certain reaction conditions, e.g., at a lower temperature such as 450° F. or less (which is less favorable to the formation of n-paraffins), more triglycerides are converted to alcohol and fatty acids than n-paraffins with the lower the temperature, the less n-paraffins formed, as exemplified with soybean oil feed which is made mainly of C18- and C16 fatty acids. Additionally, the lower the temperature, the more esters formed with the transesterification of the resulting alcohols and fatty acids. Conversely, the higher the temperature, the more alcohols formed with an increase in temperature of 50° F. (e.g., from 400° F. to 450° F.) results in an increase in the amount of alcohols formed of at least 10%.

As discussed, the hydroprocessing conditions can be selected from any parameter that influences the subsequent level of the desired product(s) in the effluent from the reactor. In one aspect, the hydroprocessing parameter is one that obtains a yield of a product in the reactant mixture, increases the yield of a product, optimizes the selectivity of products in the reactor, or is effective for a conversion of triglycerides in the reactor. In one embodiment, the hydroprocessing parameter is selected from the group consisting of a reactor temperature, a total reaction pressure and combinations thereof.

Products of the Upgrade Reactions:

The effluent from the hydroprocessing zone will comprise a liquid portion and a gaseous portion. The effluent can be passed to one or more separators/fractionators for the removal of gas phase products (e.g., CO, $CO_2$, $H_2O$, methane and propane), and separation of one or more fully and/or partially deoxygenated product fractions (e.g., n-paraffins, fatty alcohols and/or aliphatic monoesters) from the liquid portion. Different feedstocks will result in different carbon distributions of liquid products. In some embodiments, after removal of the product gases, at least a portion of the liquid effluent can be combined with the liquid effluent from the hydrotreatment of a different feedstock, e.g., petroleum feedstock. Additionally or alternately, after separating out the light end products, a recycled product stream can be recovered for us as an input stream to the upgrade reactor system.

In one embodiment, the effluent consists essentially of n-paraffins. In some embodiments, the effluent comprises at least 75 wt. % of normal paraffins (e.g., at least 80 wt. % normal paraffins). In some embodiments, the normal paraffins have from 8 to 24 carbon atoms (e.g., from 12 to 18 carbon atoms). Note that the normal paraffins can be utilized as a middle distillate fuel. However, subsequent isomerization of the normal paraffins to isoparaffins can provide a broader range of products with improved low-temperature properties such as freeze point and pour point, thereby making the process more universal and flexible.

In another embodiment, the liquid product comprises fatty alcohols, an aliphatic monoester, and normal paraffins. In another embodiment, the product is a fatty alcohol, an aliphatic monoester, or a combination thereof.

In some embodiments, the effluent comprises a fatty alcohol fraction. The fatty alcohol has from 8 and 24 carbon atoms in one embodiment, and from 8 to 18 carbon atoms in a second embodiment. In some embodiments, the effluent comprises at least 5 wt. % of a fatty alcohol (e.g., at least 10 wt. % of a fatty alcohol). In some embodiments, the effluent has a selectivity to a fatty alcohol of at least 10 wt. % (e.g., at least 15 wt. %, 20 wt. %, or 25 wt. %).

In some embodiments, the effluent comprises an aliphatic monoester fraction. The aliphatic monoester has from 18 and 36 carbon atoms in one embodiment. In some embodiments, the effluent comprises at least 4 wt. % of an aliphatic monoester (e.g., at least 7 wt. %, 10 wt. % or 13 wt. %). In some embodiments, the effluent has a selectivity to an aliphatic monoester of at least 10 wt. % (e.g., at least 12 wt. %, 15 wt. %, or 18 wt. %).

Figure 2:
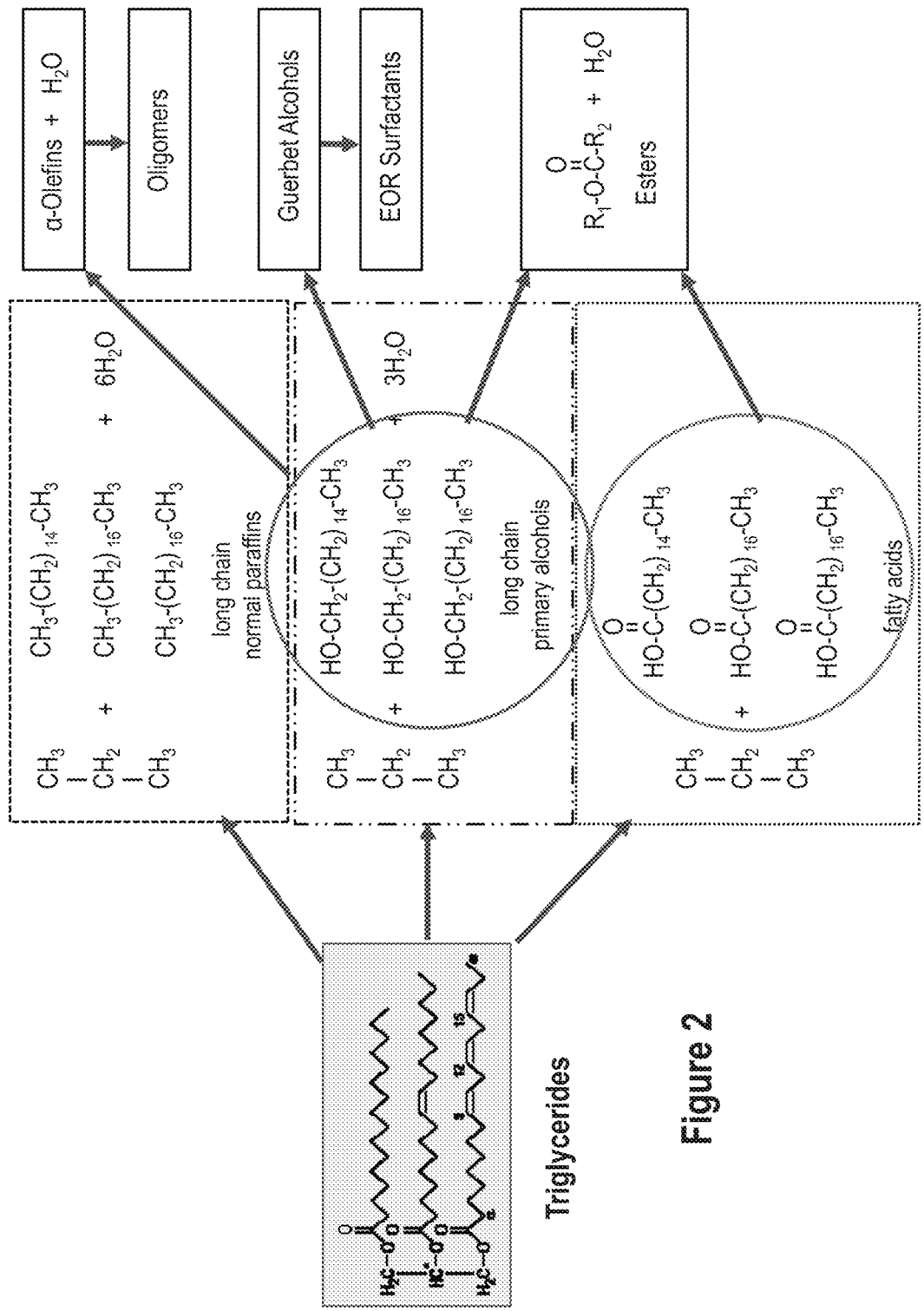
FIG. 2 is a schematic diagram showing formation of various desirable products, e.g., oligomers, esters, Guerbet alcohols and EOR (Enhanced Oil Recovery) surfactants, from the upgrading of a renewable feedstock, e.g., triglycerides.

Further Product Upgrade:

In one embodiment as shown in FIG. 2, the products generated from the hydroprocessing of a renewable feedstock after separation/recovery, can be further processed to generate various desirable products, including PAO (poly alpha olefins) or α-olefins (by dehydrating the fatty alcohol products), lubricants and bright stocks (from the oligomerizing of the PAO), and Group 3 lubricants (from co-oligomerizing of the PAO with some short chain olefins). The alcohol products can be processed forming drilling fluids, EOR (enhanced oil recovery) surfactants, and the like.

Further Product Upgrade—Catalytic Isomerization:

In some embodiments after the recovery of n-paraffins as the end-product, the upgrade process further comprises a step of catalytically isomerizing at least some of the n-paraffins to form an isomerized product comprising isoparaffins. In some embodiments, the step of catalytically isomerizing results in superior fuel properties (e.g., cloud point, pour point etc.) relative to those of the non-isomerized paraffinic product.

In some embodiments, the step of isomerizing is carried out using an isomerization catalyst. Suitable such isomerization catalysts can include, but are not limited to, Pt and/or Pd on a support. Suitable supports include, but are not limited to, zeolites CIT-1, IM-5, SSZ-20, SSZ-23, SSZ-24, SSZ-25, SSZ-26, SSZ-31, SSZ-32, SSZ-32, SSZ-33, SSZ-35, SSZ-36, SSZ-37, SSZ-41, SSZ-42, SSZ-43, SSZ-44, SSZ-46, SSZ-47, SSZ-48, SSZ-51, SSZ-56, SSZ-57, SSZ-58, SSZ-59, SSZ-60, SSZ-61, SSZ-63, SSZ-64, SSZ-65, SSZ-67, SSZ-68, SSZ-69, SSZ-70, SSZ-71, SSZ-74, SSZ-75, SSZ-76, SSZ-78, SSZ-81, SSZ-82, SSZ-83, SSZ-86, SUZ-4, TNU-9, ZSM-5, ZSM-12, ZSM-22, ZSM-23, ZSM-35, ZSM-48, EMT-type zeolites, FAU-type zeolites, FER-type zeolites, MEL-type zeolites, MFI-type zeolites, MTT-type zeolites, MTW-type zeolites, MWW-type zeolites, TON-type zeolites, other molecular sieves materials based upon crystalline aluminophosphates such as SM-3, SM-7, SAPO-11, SAPO-31, SAPO-41, MAPO-11 and MAPO-31. In some embodiments, the step of isomerizing involves a Pt and/or Pd catalyst supported on an acidic support material selected from the group consisting of beta or zeolite Y molecular sieves, silica, alumina, silica-alumina, and combinations thereof. For other suitable isomerization catalysts, see, e.g., U.S. Pat. Nos. 4,859,312; 5,158,665; and 5,300,210.

Isomerization conditions can include a temperature of from 200° F. to 900° F. (93° C. to 482° C.), e.g., from 300° F. to 800° F. (149° C. to 427° C.), or from 400° F. to 800° F. (204° C. to 427° C.); a total reaction pressure of from 15 to 3000 psig (0.1 to 20.7 MPa gauge), e.g., from 50 to 2500 psig (0.3 to 17.2 MPa gauge); a LHSV of from 0.1 to 10 $h^{-1}$, e.g., from 0.25 to 5 $h^{-1}$; and a hydrogen gas treat rate of from 0.1 to 30 MSCF/bbl, e.g., from 0.2 to 20 MSCF/bbl, or from 0.4 to 10 MSCF/bbl.

With regard to the catalytic isomerization step described above, in some embodiments, the methods described herein can be conducted by contacting the normal paraffins with a fixed stationary bed of catalyst, with a fixed fluidized bed, or with a transport bed. In one embodiment, a trickle-bed operation is employed, wherein such feed is allowed to trickle through a stationary fixed bed, typically in the presence of hydrogen. For an illustration of the operation of such catalysts, see, U.S. Pat. Nos. 6,204,426 and 6,723,889, the relevant disclosures are incorporated herein by reference.

In some embodiments, the isomerized product comprises at least 10 wt. % isoparaffins (e.g., at least 30 wt. %, 50 wt. %, or 70 wt. % isoparaffins). In some embodiments, the isomerized product has an isoparaffin to normal paraffin mole ratio of at least 5:1 (e.g., at least 10:1, 15:1, or 20:1).

In some embodiments, the isomerized product has a boiling range of from 250° F. to 1100° F. (121° C. to 593° C.), e.g., from 280° F. to 572° F. (138° C. to 300° C.), or from 250° F. to 1000° F. (121° C. to 538° C.).

In some embodiments, the isomerized product is suitable (or better suited) for use as a transportation fuel. In some such embodiments, the isomerized product is mixed or admixed with existing transportation fuels in order to create new fuels or to modify the properties of existing fuels. Isomerization and blending can be used to modulate and maintain pour point and cloud point of the fuel or other product at suitable values. In some embodiments, the normal paraffins are blended with other species prior to undergoing catalytic isomerization. In some embodiments, the normal paraffins are blended with the isomerized product.

Further Product Upgrade—Dehydration:

In one embodiment after the separation of the effluents yielding fatty alcohols as the end product, e.g., 1-hexanol and/or long chain bio-alcohols including 1-hexadecanol, etc. The alcohol products are dehydrated under dehydrating conditions forming α-olefin products, e.g., bio-1-olefins such as bio-1-hexenes or bio-1-hexadecens. The final bio-olefin products may be further processed to make bio-lubricants.

Dehydration processes to convert a bio-alcohol to α-olefin products are disclosed in US20120238788A1 and US20110288352A1, the relevant disclosures are incorporated herein by reference. In one embodiment of a dehydration process, the fatty alcohols are heated in the presence of at least a desired catalyst for a sufficient amount of time and at a sufficient temperature and optionally, with at least one purge gas. In embodiments, the optional purge gas is nitrogen, argon, or a mixture of the two gases. The reaction conditions include atmospheric pressure, a temperature of 250-420° C., and LHSV from 1 to 5 h$^{-1}$ in one embodiment. In embodiments, the heating temperatures for the dehydration range from about 300-420° C. or about 360-385° C.

The catalyst is activated alumina in one embodiment. In another embodiment, the catalyst is an equal molar combination of zinc oxide and alumina that has been treated at a temperature of 800 to 1000° C. for periods of 24 to 48 h prior, then treated with base, washed, air dried, and then treated with 0.1-20 wt. % of a chlorosilane in a hydrocarbon solvent.

In some embodiment, the fatty alcohols generated from the upgrade of renewable feedstock may be blended with other fatty alcohols, e.g., petroleum derived fatty alcohols or fatty alcohols derived from Fischer-Tropsch processes prior to the dehydration step to generate α-olefin products.

Further Product Upgrade—Oligomerization:

In one embodiment after the dehydration step, the α-olefin products generated can be further processed by oligomerizing to form a mixture of dimers, trimers, tetramers, and pentamers, optionally with some amount of other desirable higher oligomers. The oligomer products then can be hydrogenated to improve their thermal and oxidative stability. In some embodiments dehydrating, oligomerizing, and hydrogenating are each carried out in the presence of a dehydration catalyst, oligomerization catalyst, and a hydrogenation catalyst, respectively. In some embodiments, dehydrating, oligomerizing, and hydrogenating may be carried out in a different reaction zone. In certain embodiments, two or more of dehydrating, oligomerizing, and hydrogenating may be carried out in the same reaction zone. Oligomerization processes to convert the α-olefin products are disclosed in US20110288352A1, the relevant disclosures are incorporated herein by reference.

In one embodiment of an oligomerization step, the α-olefin products generated above are reacted over a heterogeneous acidic catalyst, such as sulfonic acid resin, solid phosphoric acid, or acidic zeolite, or any other suitable catalyst at moderate temperatures (e.g., 100-300° C.) and pressures (e.g., 0-1000 psig) to form a blend of co-oligomers of the resulting α-olefins with light olefins such as butene(s). Heterogeneous or homogenous oligomerization catalysts can be used are described in G. Busca, "Acid Catalysts in Industrial Hydrocarbon Chemistry" Chem Rev 2007 (107) 5366-5410. Other catalysts include acidic solid phase catalysts such as alumina and zeolites (see, e.g., U.S. Pat. Nos. 3,997,621; 4,663,406; 4,612,406; 4,864,068; and 5,962,604). In certain embodiments acidic resin catalysts may be employed such as Amberlyst-35 catalysts.

The oligomerization conditions may be optimized as described herein to limit production of light or heavy components which simplifies the downstream fractionation step, e.g., by appropriate selection of catalyst, reaction time, temperature, pressure, etc. during the oligomerization step, to meet specific requirements of the desirable lubricants and bright stock products. Additionally, lighter and/or heavier fractions from the oligomerization reaction may be removed (by, e.g., distillation, etc.) prior to further processing to provide a hydrogenation feedstock, e.g., a jet fuel blend stock. Alternatively, lighter and heavier fraction may be separated after hydrogenation/hydrotreating. Various methods can be used for controlling the molecular weight distribution of the resulting oligomers, including methods which form primarily dimers including isooctene (see, e.g., U.S. Pat. No. 6,689,927), trimers (see, e.g., PCT Pat. Appl. Pub. No. WO 2007/091862), and tetramers and pentamers (see e.g., U.S. Pat. No. 6,239,321), the relevant disclosures are incorporated herein by reference.

Further Product Upgrade—Co-oligomerization:

In some cases, less branched olefins produced from a dehydration reaction may be smaller than desired, e.g., C8 olefins. In one embodiment, the smaller oligomers C4-C8 olefins may be separated from the product mixture, then led to an oligomerization reaction zone to co-oligomerize with other long chain α-olefins, forming Group 3 lubricant products. In another embodiment, the resulting long chain α-olefin olefins may be separated from the product mixture, then led to an oligomerization reaction zone to co-oligomerize with some light olefins such as butene(s), forming Group 3 lubricant products.

EXAMPLES

The following illustrative examples are intended to be non-limiting.

Example 1

A soybean feed having an API gravity of 21.6 (0.9223 g/mL) is employed as the feedstock. The triglycerides of soybean oil are derived mainly from five fatty acids (see, e.g., D. Firestone, *Physical and Chemical Characteristics of Oils, Fats, and Waxes*, 2$^{nd}$ Edition, 2006, AOCS Press, 149). Table 1 discloses the representative ranges of these fatty acids in soybean oil.

TABLE 1

| Fatty acid | Carbon atoms:Double bonds | Weight Percent |
|---|---|---|
| Palmitic acid | 16:0 | 9.7 to 13.3 |
| Stearic acid | 18:0 | 3.0 to 5.4 |
| Oleic acid | 18:1 | 17.7 to 28.5 |
| Linoleic acid | 18:2 | 49.8 to 57.1 |
| α-Linoleic acid | 18:3 | 5.5 to 9.5 |

Examples 2-8

The soybean oil feed from Example 1 was tested under hydroprocessing conditions in a single reactor over a promoted catalyst based on a Ni—Mo—W-maleate catalyst precursor (per Example 1 of U.S. Pat. No. 7,807,599) and sulfided with dimethyl disulfide gas (per Example 6 of U.S. Pat. No. 7,807,599). The reactor conditions included a hydrogen gas rate of 8.0 MSCF/bbl and a LHSV of 1.0 h$^{-1}$. Additional hydroprocessing conditions (reactor temperature and pressure) are set forth in Tables 2 and 3.

The composition of the whole product was determined by gas chromatography (GC) and is set forth in wt. % in Table 2. All liquid paraffinic products were normal paraffins as determined by GC with negligible amounts of isoparaffins formed. Methane and propane were essentially the only other light hydrocarbon products. Water, carbon monoxide (CO), and carbon dioxide ($CO_2$) were by-products from hydrodeoxygenation, hydrodecarbonylation and/or hydrodecarboxylation.

TABLE 2

| | Ex. 2 | Ex. 3 | Ex. 4 | Ex. 5 | Ex. 6 | Ex. 7 | Ex. 8 |
|---|---|---|---|---|---|---|---|
| Reaction conditions | | | | | | | |
| Temperature °F. | 400 | 450 | 500 | 550 | | | |
| Pressure, psig | 1900 | 1900 | 1900 | 1900 | | | |
| Unconverted triglycerides | 75.4 | 10.9 | <0.5 | <0.5 | <0.5 | <0.5 | <0.5 |
| Products | | | | | | | |
| n-$C_{18}$ paraffin | 4.8 | 27.9 | 54.2 | 45.1 | 46.0 | 35.1 | 23.1 |
| n-$C_{17}$ paraffin | 0.7 | 12.0 | 19.2 | 26.6 | | | |
| n-$C_{16}$ paraffin | 0.6 | 3.5 | 6.6 | 6.4 | 5.7 | 4.8 | 3.8 |
| n-$C_{15}$ paraffin | 0.1 | 1.4 | 2.3 | 3.5 | | | |
| $C_{18}$ alcohol | 5.8 | 9.9 | — | — | — | — | — |
| $C_{16}$ alcohol | 0.6 | 1.2 | — | — | — | — | — |
| $C_{18}$ acid | 2.7 | 4.1 | — | — | — | — | — |
| $C_{16}$ acid | 0.3 | 0.4 | — | — | — | — | — |
| $C_{18}$-$C_{18}$ ester | 3.5 | 10.2 | — | — | — | — | — |
| $C_{18}$-$C_{16}$ ester | 0.9 | 2.6 | — | — | — | — | — |
| $C_{16}$-$C_{16}$ ester | 0.1 | 0.2 | — | — | — | — | — |
| Unknown heavies | 1.6 | 2.5 | — | — | — | — | — |
| Propane | 1.2 | 4.4 | 4.9 | 5.0 | 4.9 | 5.0 | 4.8 |
| Methane | 0.02 | 0.04 | 0.2 | 0.8 | 0.1 | 0.2 | 1.1 |
| $H_2O$ | 1.6 | 6.6 | 9.8 | 9.7 | 8.9 | 7.5 | 7.4 |
| CO | 0.1 | 0.7 | 0.4 | 0.4 | 2.0 | 2.1 | 1.8 |
| $CO_2$ | 0.1 | 1.5 | 2.4 | 2.5 | 2.3 | 3.8 | 4.3 |

With reference to the examples hydroprocessed at 1900 psig and temperatures of 500° F. and 550° F. (Examples 4 and 5), both the $C_{15}/C_{16}$ n-paraffin and $C_{17}/C_{18}$ n-paraffin product ratios were 0.35 by weight at 500° F. (Example 4). At 550° F. (Example 5), the $C_{15}/C_{16}$ n-paraffin product ratio increased to 0.55 by weight while the $C_{17}/C_{18}$ n-paraffin product ratio increased to 0.59 by weight. The increase in the $C_{15}/C_{16}$ and $C_{17}/C_{18}$ n-paraffin product ratios indicated enhanced selectivity of this catalyst for hydrodecarboxylation and/or hydrodecarbonylation (making $C_{15}$ and $C_{17}$ n-paraffins as well as CO and $CO_2$ plus $H_2O$) over hydrodeoxygenation (making $C_{16}$ and $C_{18}$ n-paraffins as well as water) at higher reaction temperatures. Accordingly, a slightly higher (CO+$CO_2$)/$H_2O$ product ratio by weight was achieved at higher temperatures, also reflecting some enhanced selectivity for hydrodecarboxylation and/or hydrodecarbonylation over hydrodeoxygenation.

With reference to the examples hydroprocessed at 1000 psig, the $C_{15}/C_{16}$ n-paraffin product ratio by weight at 500° F. (Example 6) was 0.56 while the $C_{17}/C_{18}$ n-paraffin ratio was 0.59 by weight. At 550° F. (Example 7), the $C_{15}/C_{16}$ n-paraffin product ratio increased to 1.02 by weight while the $C_{17}/C_{18}$ n-paraffin product ratio increased to 1.04 by weight. In addition, at 650° F. (Example 8), the $C_{15}/C_{16}$ n-paraffin product ratio increased to 1.80 by weight while the $C_{17}/C_{18}$ n-paraffin product ratio increased to 2.03 by weight. The increase in the $C_{15}/C_{16}$ and $C_{17}/C_{18}$ n-paraffin product ratios indicated enhanced selectivity of this catalyst for hydrodecarboxylation and/or hydrodecarbonylation (making $C_{15}$ and $C_{17}$ n-paraffins as well as CO and $CO_2$ plus $H_2OO$) over hydrodeoxygenation (making $C_{16}$ and $C_{18}$ n-paraffins as well as water) at higher reaction temperatures. Accordingly, higher (CO+$CO_2$)/$H_2OO$ product ratios were achieved at higher temperatures, also reflecting the enhanced selectivity for hydrodecarboxylation and/or hydrodecarbonylation over hydrodeoxygenation.

Furthermore, in comparing the results of Examples 4 and 5 (run at 1900 psig) to those of Example 6 and 7 (run at 1000 psig) respectively, enhanced selectivity for hydrodecarboxylation and/or hydrodecarbonylation over hydrodeoxygenation was achieved at lower reaction pressure, leading to further reduction of hydrogen consumption.

The conversion rate of triglycerides and product selectivity of the hydroprocessing runs are set forth in Table 3.

TABLE 3

| | Ex. 2 | Ex. 3 | Ex. 4 | Ex. 5 | Ex. 6 | Ex. 7 | Ex. 8 |
|---|---|---|---|---|---|---|---|
| Reaction conditions | | | | | | | |
| Temperature, °F. | 400 | 450 | 500 | 550 | 500 | 550 | 650 |
| Reaction Pressure, psig | 1900 | 1900 | 1900 | 1900 | 1000 | 1000 | 1000 |
| Products | | | | | | | |
| Conversion of triglycerides, wt. % | 24.6 | 89.1 | >99.5 | >99.5 | >99.5 | >99.5 | >99.5 |

TABLE 3-continued

|  | Ex. 2 | Ex. 3 | Ex. 4 | Ex. 5 | Ex. 6 | Ex. 7 | Ex. 8 |
|---|---|---|---|---|---|---|---|
| Product Selectivity, % | | | | | | | |
| n-$C_{18}$ paraffin | 19.3 | 31.3 | 54.2 | 45.1 | 46.0 | 35.1 | 23.1 |
| n-$C_{17}$ paraffin | 3.0 | 13.4 | 19.2 | 26.6 | 26.9 | 36.6 | 46.9 |
| n-$C_{16}$ paraffin | 2.4 | 3.9 | 6.6 | 6.4 | 5.7 | 4.8 | 3.8 |
| n-$C_{15}$ paraffin | 0.3 | 1.6 | 2.3 | 3.5 | 3.2 | 4.9 | 6.8 |
| $C_{18}$ alcohol | 23.7 | 11.2 | — | — | — | — | — |
| $C_{16}$ alcohol | 2.6 | 1.3 | — | — | — | — | — |
| $C_{18}$ acid | 11.1 | 4.7 | — | — | — | — | — |
| $C_{16}$ acid | 1.2 | 0.5 | — | — | — | — | — |
| $C_{18}$-$C_{18}$ ester | 14.1 | 11.5 | — | — | — | — | — |
| $C_{18}$-$C_{16}$ ester | 3.7 | 2.9 | — | — | — | — | — |
| $C_{16}$-$C_{16}$ ester | 0.2 | 0.2 | — | — | — | — | — |
| Unknown heavies | 6.4 | 2.8 | — | — | — | — | — |
| Propane | 4.9 | 4.9 | 4.9 | 5.0 | 4.9 | 5.0 | 4.8 |
| Methane | 0.1 | 0.1 | 0.2 | 0.8 | 0.1 | 0.2 | 1.1 |
| $H_2O$ | 6.4 | 7.4 | 9.8 | 9.7 | 8.9 | 7.5 | 7.4 |
| CO | 0.4 | 0.8 | 0.4 | 0.4 | 2.0 | 2.1 | 1.8 |
| $CO_2$ | 0.2 | 1.7 | 2.4 | 2.5 | 2.3 | 3.8 | 4.3 |

Examples 9-12

The soybean oil feed from Example 1 was tested under hydroprocessing conditions at several temperatures in a single-stage reactor over a promoted hydroprocessing catalyst prepared as disclosed in US20090298677A1, e.g., an alumina-supported Ni—Mo catalyst available from Chevron Lummus Global, having a median pore size of about 8 nm and specific surface area of about 180 m²/g. The reactor conditions include a total reaction pressure of 1900 psig (13.1 MPa gauge), a hydrogen gas rate of 8.0 MSCF/bbl, and a LHSV of 1.0 h$^{-1}$.

The composition of the whole product was determined by gas chromatography (GC) and is set forth in wt. % in Table 4. All liquid paraffinic products were normal paraffins as determined by GC with negligible amounts of isoparaffins formed. Methane and propane were essentially the only other hydrocarbon products. Water, carbon monoxide (CO), and carbon dioxide ($CO_2$) were by-products from hydrodeoxygenation, hydrodecarbonylation and/or hydrodecarboxylation.

TABLE 4

|  | Ex. 9 | Ex. 10 | Ex. 11 | Ex. 12 |
|---|---|---|---|---|
| Reaction conditions | | | | |
| Reaction Temperature, °F. | 400 | 450 | 500 | 550 |
| Reaction Pressure, psig | 1900 | 1900 | 1900 | 1900 |
| Products, wt. % | | | | |
| Unconverted triglycerides | 42.4 | 0.2 | <0.5 | <0.5 |
| n-$C_{18}$ paraffin | 1.1 | 14.9 | 68.7 | 69.0 |
| n-$C_{17}$ paraffin | 0.1 | 1.5 | 5.3 | 4.8 |
| n-$C_{16}$ paraffin | 0.3 | 1.4 | 8.3 | 8.5 |
| n-$C_{15}$ paraffin | 0 | 0 | 0.6 | 0.5 |
| $C_{18}$ alcohol | 19.6 | 42.5 | — | — |
| $C_{16}$ alcohol | 0.5 | 4.6 | — | — |
| $C_{18}$ acid | 0.4 | 0.4 | — | — |
| $C_{16}$ acid | 0 | 0 | — | — |
| $C_{18}$-$C_{18}$ ester | 20.9 | 16.7 | — | — |
| $C_{18}$-$C_{16}$ ester | 5.5 | 4.0 | — | — |
| $C_{16}$-$C_{16}$ ester | 0.4 | 0.2 | — | — |
| Unknown heavies | 2.7 | 1.5 | — | — |
| Propane | 2.8 | 4.9 | 4.9 | 4.9 |
| Methane | 0 | 0 | 0.1 | 0.3 |
| $H_2O$ | 3.3 | 7.0 | 11.4 | 11.8 |
| CO | 0 | 0 | 0 | 0 |
| $CO_2$ | 0.1 | 0.3 | 0.6 | 0.3 |

The conversion rate of triglycerides and product selectivity of the hydroprocessing runs with supported catalysts are set forth in Table 5.

TABLE 5

|  | Ex. 9 | Ex. 10 | Ex. 11 | Ex. 12 |
|---|---|---|---|---|
| Reaction conditions | | | | |
| Reaction Temperature, °F. | 400 | 450 | 500 | 550 |
| Reaction Pressure, psig | 1900 | 1900 | 1900 | 1900 |
| Conversion of triglycerides, wt. % | 57.6 | 99.8 | >99.5 | >99.5 |
| Product Selectivity, % | | | | |
| n-$C_{18}$ paraffin | 1.9 | 15.0 | 68.7 | 69.0 |
| n-$C_{17}$ paraffin | 0.1 | 1.5 | 5.3 | 4.8 |
| n-$C_{16}$ paraffin | 0.5 | 1.4 | 8.3 | 8.5 |
| n-$C_{15}$ paraffin | 0 | 0 | 0.6 | 0.5 |
| $C_{18}$ alcohol | 34.0 | 42.6 | — | — |
| $C_{16}$ alcohol | 0.8 | 4.6 | — | — |
| $C_{18}$ acid | 0.7 | 0.4 | — | — |
| $C_{16}$ acid | 0 | 0 | — | — |
| $C_{18}$-$C_{18}$ ester | 36.2 | 16.7 | — | — |
| $C_{18}$-$C_{16}$ ester | 9.5 | 4.0 | — | — |
| $C_{16}$-$C_{16}$ ester | 0.6 | 0.2 | — | — |
| Unknown heavies | 4.7 | 1.5 | — | — |
| Propane | 4.9 | 4.9 | 4.9 | 4.9 |
| Methane | 0.1 | 0.1 | 0.1 | 0.3 |
| $H_2O$ | 5.8 | 7.0 | 11.4 | 11.8 |
| CO | 0 | 0 | 0 | 0 |
| $CO_2$ | 0.3 | 0.3 | 0.6 | 0.3 |

Examples 13-14

The soybean oil feed from Example 1 was tested under hydroprocessing conditions in a single reactor with a pre-sulfided promoted self-supported catalyst (as used in Examples 2-8) and a pre-sulfided promoted supported catalyst (as used in Examples 9-12), with reaction conditions at 550° F., 1000 psig, 1.0 h$^{-1}$ LHSV, and $H_2$ rate of 8000 scf/bbl feed. All the triglycerides in the feed were converted and paraffins were the only components in the liquid products. Table 6 presents the SimDis (simulated distillation by gas chromatography) of the diesel products from the two examples. The promoted self-supported catalyst is more selective than the promoted supported catalyst for hydrodecarboxylation-hydrodecarbonylation reactions.

TABLE 6

|  | Example 13 Self-supported catalyst | Example 14 Supported catalyst |
|---|---|---|
| n-$C_{18}$ paraffin | 54 | 79 |
| n-$C_{17}$ paraffin | 35 | 6 |
| n-$C_{16}$ paraffin | 7 | 10 |
| n-$C_{15}$ paraffin | 4 | 1 |

Examples 15-16

The soybean oil feed from Example 1 was tested under hydroprocessing conditions in a single reactor with a pre-sulfided promoted self-supported catalyst (as used in Examples 2-8) but under different total reaction pressures 1000 psig and 500 psig, with other reaction conditions including a temperature of 600° F., 0.5 h$^{-1}$ LHSV, and H$_2$ rate of 8000 scf/bbl feed. All the triglycerides in the feed were converted and paraffins were the only components in the liquid products. Table 7 presents the SimDis (simulated distillation by gas chromatography) of the diesel products from the two examples. Lower pressure is more favorable for hydrodecarboxylation-hydrodecarbonylation reactions.

TABLE 7

|  | Example 15 1000 psig | Example 16 500 psig |
|---|---|---|
| n-$C_{18}$ paraffin | 41.9 | 29.8 |
| n-$C_{17}$ paraffin | 46.5 | 59.1 |
| n-$C_{16}$ paraffin | 5.8 | 4.3 |
| n-$C_{15}$ paraffin | 5.8 | 6.9 |

Examples 17-18

The soybean oil feed from Example 1 was tested under hydroprocessing conditions in a single reactor with an unsulfided promoted self-supported catalyst precursor (as used in Examples 2-8, but not sulfided), and with sulfided promoted self-supported catalyst (as used in Examples 2-8) but under the same reaction conditions including a temperature of 550° F., a pressure of 1000 psig, 1.0 h$^{-1}$ LHSV, and H$_2$ rate of 8000 scf/bbl feed. All the triglycerides in the feed were converted and paraffins were the only components in the liquid products. Table 8 presents the SimDis (simulated distillation by gas chromatography) of the diesel products from the two examples. Sulfided promoted self-supported catalyst is more active than the unsulfided version. However, it is noted that the reaction proceeded even with unsulfided promoted catalyst precursors.

TABLE 8

|  | Example 17 pre-sulfided | Example 18 Unsulfided |
|---|---|---|
| n-$C_{18}$ paraffin | 54 | 71 |
| n-$C_{17}$ paraffin | 35 | 18 |
| n-$C_{16}$ paraffin | 7 | 10 |
| n-$C_{15}$ paraffin | 4 | 2 |

Example 19

The soybean oil feed from Example 1 was tested under hydroprocessing conditions (500 or 550° F., 1000 psig, 1.0 h$^{-1}$ LHSV, and H$_2$ rate of 8000 scf/bbl feed) in a single reactor with a noble metal, amorphous catalyst from Chevron Lummus Global under the trade name of ICR-419. It is noted that the noble metal catalyst does not appear to be efficient for hydrodecarboxylation and hydrodecarbonylation, as shown by the low conversions of triglycerides of 57 wt. % at 500° F. and 88 wt. % at 550° F., respectively, and with relatively low formation of n-paraffins compared to the amount of fatty alcohol and esters formed.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. As used herein, the term "comprising" means including elements or steps that are identified following that term, but any such elements or steps are not exhaustive, and an embodiment can include other elements or steps.

Unless otherwise specified, the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. A process for the catalytic upgrade of a feedstock comprising renewable materials consisting essentially of triglycerides, the process comprising:
   contacting the feedstock under hydroprocessing conditions with at least a promoted catalyst to form a liquid effluent and a gaseous product, the promoted catalyst is selected from the group consisting of a self-supported catalyst, a supported catalyst and combinations thereof, the catalyst comprising at least a Group VIB metal selected from the group consisting of molybdenum and tungsten, at least a Group VIII metal selected from the group consisting of cobalt and nickel, the promoter being selected from the group consisting of hydroxy-(di)-carboxylic acids with steric configurations and having the structure of:

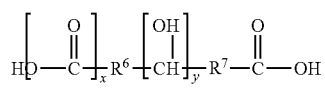

where x is 1 or 0, y is 1 or 0, and $R^6$ and $R^7$ are a saturated, unsaturated, cyclic, acyclic, aromatic, alcoholic, or branched or unbranched hydrocarbon group, with $R^6$ and $R^7$ being $(CH)_{2m}(CH_2)_n$ with m and n as ≥0 integers; and recovering the liquid effluent comprising at least one of normal paraffins, fatty alcohols, aliphatic monoesters and combinations thereof, wherein the hydroprocessing conditions are selected substantially according to any of:

a reaction temperature of at least 446° F. (230° C.) for a triglycerides conversion rate of at least 50%;

a reaction temperature of at least 446° F. (230° C.) and a total reaction pressure from 50 to 3000 psig (0.35 to 20.7 MPa gauge) for the liquid effluent to have a normal paraffins concentration of at least 30 wt. %;

a reaction temperature of 302° F. to 554° F. (150° C. to 290° C.) and a total reaction pressure from 50 to 3000 psig (0.35 to 20.7 MPa gauge) for the liquid effluent to have a fatty alcohols concentration of at least 5 wt. %; or a reaction temperature of 302° F. to 554° F. (150° C. to 290° C.) and a total reaction pressure from 50 to 3000 psig (0.35 to 20.7 MPa gauge) for the liquid effluent to have an aliphatic monoesters concentration of at least 5 wt. %.

2. The process of claim 1, wherein the promoter is present in an amount of at least 0.05 molar times of the total number of moles of the metals of Group VIB and Group VIII.

3. The process of claim 1, wherein the feedstock consists essentially of renewable materials.

4. The process of claim 3, wherein the renewable materials are based on vegetable oils and/or animal fats.

5. The process of claim 1, wherein the feedstock comprises a mixture of renewable materials and petroleum feedstock in an amount of 1 to 99 wt. % of petroleum feedstock, with the remainder renewable materials.

6. The process of claim 1, wherein the catalytic upgrade is carried out in a single reactor system.

7. The process of claim 1, wherein the catalytic upgrade is carried out in a reactor system comprising at least two reactors in series employing the same or different promoted catalysts.

8. The process of claim 1, wherein the catalytic upgrade is carried out in a layered reactor system with the first layer containing a promoted self-supported catalyst and the second layer containing a promoted supported catalyst at a volume ratio of 5:95 to 95:5 of promoted self-supported catalyst to promoted supported catalyst.

9. The process of claim 1, wherein the catalyst is brought into contact with the feedstock without being pre-sulfided.

10. The process of claim 9, wherein the catalyst is brought into contact with the feedstock without any sulfiding agents being added or present in the feedstock.

11. The process of claim 9, wherein the catalyst is brought into contact with the feedstock with at least a sulfiding agent added or being present in the feedstock.

12. The process of claim 1, wherein the catalyst is a catalyst precursor that has been pre-sulfided before being brought into contact with the feedstock.

13. The process of claim 1, wherein the catalyst is a supported catalyst.

14. The process of claim 13, wherein the supported catalyst has an average pore size of 1-10 nm and a surface area of 20-400 m²/g.

15. The process of claim 1, wherein the catalyst is a self-supported catalyst.

16. The process of claim 15, wherein the self-supported catalyst is derived from a self-supported mixed metal sulfide catalyst precursor having a molar ratio of Ni/W of 1.62≤Ni/W≤2.5, a molar ratio of W/Mo is in the range of 0.5≤W/Mo≤6.0, and a molar ratio of Ni/(Mo+W) in the range of 0.57<Ni/(Mo+W)<2.1.

17. The process of claim 15, wherein the self-supported catalyst is derived from a self-supported mixed metal sulfide catalyst precursor having a molar ratio of nickel, molybdenum and tungsten in relative proportions within a compositional range defined by four points ABCD of a ternary phase diagram, with molar fractions of the four points ABCD defined by A($Ni_x$=0.36, $Mo_x$=0.41, $W_x$=0.22); B($Ni_y$=0.45, $Mo_y$=0.36, $W_y$=0.18); C($Ni_z$=0.58, $Mo_z$=0.06, $W_z$=0.36), and D ($Ni_w$=0.68, $Mo_w$=0.05, $W_w$=0.27).

18. The process of claim 1, wherein the hydroprocessing conditions are selected to include a temperature of at least 500° F. (288° C.) for the recovered liquid effluent to a normal paraffins concentration of at least 90 wt. %.

19. The process of claim 1, wherein the hydroprocessing conditions are selected to include a total reaction pressure of 1200 psi or less for the recovered liquid effluent to a normal paraffins concentration of at least 90 wt. %.

20. The process of claim 1, wherein the hydroprocessing conditions are selected to include a temperature of at least 550° F. (288° C.) and a total reaction pressure of 1200 psi or less for the recovered liquid effluent to have more n-C17 paraffin over n-C18 paraffin.

21. The process of claim 1, further comprising:
recovering a normal paraffins product from the liquid effluent;
catalytically-isomerizing at least a portion of the normal paraffins to form an isomerized product comprising iso-paraffins.

22. A process for the catalytic upgrade of a feedstock comprising renewable materials consisting essentially of triglycerides, the process comprising:
contacting the feedstock under hydroprocessing conditions with at least a promoted catalyst to form a liquid effluent and a gaseous product, the catalyst is selected from the group consisting of a self-supported catalyst, a supported catalyst and combinations thereof, the catalyst comprising at least a Group VIB metal selected from the group consisting of molybdenum and tungsten, a Group VIII metal selected from the group consisting of cobalt and nickel, the promoter being selected from the group consisting of hydroxy-(di)-carboxylic acids with steric configurations and having the structure of:

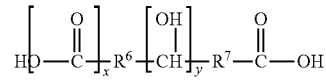

where x is 1 or 0, y is 1 or 0, and $R^6$ and $R^7$ are a saturated, unsaturated, cyclic, acyclic, aromatic, alcoholic, or branched or unbranched hydrocarbon group, with $R^6$ and $R^7$ being $(CH)_{2m}(CH_2)_n$ with m and n as ≥0 integers; and recovering the liquid effluent having a fatty alcohols concentration of at least 5 wt. % and an aliphatic monoesters concentration of at least 5 wt. %;

wherein the hydroprocessing conditions include a temperature of from 302° F. to 554° F. (150° C. to 290° C.) and a total reaction pressure from 50 to 3000 psig (0.35 to 20.7 MPa gauge).

23. The process of claim 22, further comprising:
recovering a fatty alcohols product from the liquid effluent.

24. The process of claim 23, further comprising:
dehydrating the fatty alcohols product under dehydrating conditions in the presence of at least a catalyst for a sufficient amount of time and at a sufficient temperature forming α-olefin products.

25. The process of claim 24, wherein the α-olefin products comprise bio-1-olefin.

26. The process of claim 23, further comprising blending into the fatty alcohols product other fatty alcohols prior to the dehydration step to generate α-olefin products.

27. The process of claim 26, wherein the other fatty alcohols comprised at least one of petroleum derived fatty alcohols, fatty alcohols derived from Fischer-Tropsch processes, and combinations thereof.

28. The process of claim 24, further comprising:
reacting the α-olefin products over a heterogeneous acidic catalyst at a temperature of 100-300° C. and under pressure of 0-1000 psig to form a blend of oligomers.

29. The process of claim 28, wherein the heterogeneous acidic catalyst is selected from the group consisting of sulfonic acid resin, solid phosphoric acid, acidic zeolite, acidic solid phase catalysts, acidic resin catalysts, ionic liquids, and combinations thereof.

30. The process of claim 28, further comprising:
separating C4-C16 oligomers of butenes from the blend of C4-C16 oligomers of butenes;
co-oligomerizing the α-olefin products with light olefins to form Group 3 lubricant products.

31. A process to optimize hydrogen consumption in the catalytic upgrade of a feedstock comprising renewable materials consisting essentially of triglycerides, the process comprising:
contacting the feedstock under hydroprocessing conditions with at least a promoted catalyst to form a liquid effluent and a gaseous product, the promoted catalyst is selected from the group consisting of a self-supported catalyst, a supported catalyst and combinations thereof, the catalyst comprising at least a Group VIB metal selected from the group consisting of molybdenum and tungsten, a Group VIII metal selected from the group consisting of cobalt and nickel, the promoter being selected from the group consisting of hydroxy-(di)-carboxylic acids with steric configurations, having the structure:

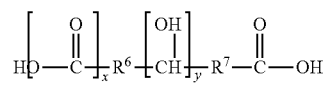

where x is 1 or 0, y is 1 or 0, and $R^6$ and $R^7$ are a saturated, unsaturated, cyclic, acyclic, aromatic, alcoholic, branched or unbranched hydrocarbon group, with $R^6$ and $R^7$ being $(CH)_{2m}(CH_2)_n$ with m and n as ≥0 integers;
the hydroprocessing conditions including a reactor temperature of from 446° F. to 752° F. (230° C. to 400° C.) and a total reaction pressure from 50 to 3000 psig (0.35 to 20.7 MPa gauge); and
recovering the liquid effluent having a normal paraffins concentration of at least 30 wt. %,
wherein the hydroprocessing conditions are adjusted by any of: increasing the reactor temperature of at least 50° F., decreasing the total reaction pressure of at least 100 psi, and combinations thereof for a reduction in hydrogen consumption in the process of at least 10 SCF/barrel of feedstock.

32. The process of claim 31, wherein every increase in reactor temperature of at least 50° F., or every decrease in the total reaction pressure of at least 100 psi results in a reduction in hydrogen consumption in the process of at least 20 SCF/barrel of feedstock.

* * * * *